United States Patent
Weinstein et al.

(10) Patent No.: US 9,629,561 B2
(45) Date of Patent: Apr. 25, 2017

(54) MONITORING AND DIAGNOSTIC SYSTEMS AND METHODS

(71) Applicant: KYMA MEDICAL TECHNOLOGIES LTD., Kfar Saba (IL)

(72) Inventors: Uriel Weinstein, Mazkeret Batia (IL); Assaf Bernstein, Givat Nilly (IL); Eyal Cohen, Gedera (IL)

(73) Assignee: KYMA MEDICAL TECHNOLOGIES LTD. (IL)

( * ) Notice: Subject to any disclaimer, the term of this patent is extended or adjusted under 35 U.S.C. 154(b) by 433 days.

(21) Appl. No.: 14/379,125

(22) PCT Filed: Feb. 15, 2013

(86) PCT No.: PCT/IB2013/000663
§ 371 (c)(1),
(2) Date: Aug. 15, 2014

(87) PCT Pub. No.: WO2013/121290
PCT Pub. Date: Aug. 22, 2013

(65) Prior Publication Data
US 2015/0025333 A1    Jan. 22, 2015

Related U.S. Application Data

(60) Provisional application No. 61/599,223, filed on Feb. 15, 2012.

(51) Int. Cl.
*A61B 5/05* (2006.01)
*A61B 5/0215* (2006.01)
(Continued)

(52) U.S. Cl.
CPC ...... *A61B 5/02158* (2013.01); *A61B 5/04005* (2013.01); *A61B 5/0537* (2013.01);
(Continued)

(58) Field of Classification Search
CPC ............ A61B 5/02158; A61B 5/04005; A61B 5/0537; A61B 5/4875; A61B 5/4878; A61B 5/686; A61B 5/6876
See application file for complete search history.

(56) References Cited

U.S. PATENT DOCUMENTS

2002/0151816 A1   10/2002   Rich et al.
2007/0156057 A1   7/2007    Cho et al.
(Continued)

FOREIGN PATENT DOCUMENTS

| CN | 101032400 A | 9/2007 |
| CN | 101516437 A | 8/2009 |
| WO | 2012/011065 A1 | 1/2012 |

OTHER PUBLICATIONS

Supplementary European Search Report, mailed Mar. 7, 2016 for EP Application No. 13748671.8, filed Feb. 15, 2013.
(Continued)

*Primary Examiner* — Mark Remaly
(74) *Attorney, Agent, or Firm* — Cooley LLP

(57) ABSTRACT

An apparatus, a system, and a method for monitoring and/or performing a diagnosis. A first implantable device measures a property of a first tissue in a body and includes a housing. The housing includes a first processing circuitry for causing the first implantable device to measure the property of the first tissue. A second implantable device for measures a property of a second tissue in the body and includes a housing. The housing includes a second processing circuitry for causing the second implantable device to measure the property of the second tissue using at least one sensor. The second implantable device is communicatively coupled to the first implantable device and provides information about the measured property of the second tissue to at least one of
(Continued)

the following: the first implantable device and at least one processing device disposed externally to the body.

12 Claims, 12 Drawing Sheets

(51) Int. Cl.
*A61B 5/04* (2006.01)
*A61B 5/00* (2006.01)
*A61B 5/053* (2006.01)

(52) U.S. Cl.
CPC .......... *A61B 5/4875* (2013.01); *A61B 5/4878* (2013.01); *A61B 5/686* (2013.01); *A61B 5/6876* (2013.01)

(56) References Cited

U.S. PATENT DOCUMENTS

| | | |
|---|---|---|
| 2007/0162090 A1 | 7/2007 | Penner |
| 2008/0200802 A1 | 8/2008 | Bhavaraju et al. |
| 2010/0081895 A1 | 4/2010 | Zand |
| 2010/0312301 A1 | 12/2010 | Stahmann |
| 2011/0004076 A1 | 1/2011 | Janna et al. |
| 2011/0125207 A1 | 5/2011 | Nabutovsky et al. |
| 2011/0130800 A1 | 6/2011 | Weinstein et al. |
| 2012/0029323 A1 | 2/2012 | Zhao |

OTHER PUBLICATIONS

International Search Report and Written Opinion, mailed Nov. 26, 2013 for Application No. PCT/IB13/00663, filed Feb. 15, 2013.

MONITORING AND DIAGNOSTIC SYSTEMS AND METHODS

RELATED APPLICATIONS

The present application is a 371 National Stage Application of PCT application no. PCT/IB2013/000663, having an international filing date of Feb. 15, 2013, claiming priority to and benefit of U.S. provisional patent application No. 61/599,223, filed Feb. 15, 2012; both disclosures of which are herein incorporated by reference in their entireties

CROSS-REFERENCE TO RELATED APPLICATIONS

The present application claims priority to U.S. Provisional Patent Application No. 61/599,223 to Weinstein et al., filed Feb. 15, 2012, and entitled "Monitoring and Diagnostic Systems and Methods," and incorporates its disclosure herein by reference in its entirety.

The present application also relates to co-owned/co-pending U.S. patent application Ser. No. 12/759,715 to Weinstein et al., filed Apr. 14, 2010, and entitled "Microwave Monitoring of Heart Function", which claims priority to the International Patent Application No. PCT/IB2009/055438, filed Dec. 1, 2009, and incorporates the disclosures of these applications herein by reference in their entireties.

TECHNICAL FIELD

In some embodiments, the current subject matter generally relates to monitoring a diagnosis of cardiovascular and/or cardiopulmonary functions in the body of a patient, and in particular, the current subject matter relates to monitoring of cardiovascular and/or cardiopulmonary functions using microwave and/or radio-frequency monitoring and/or sensing systems.

BACKGROUND

Heart-related conditions and diseases affect a significant percentage of population in today's world. Some causes of such conditions/diseases are genetic predispositions, poor dietary habits, smoking, lack of physical activity, etc. These conditions/diseases include myocardial infraction, heart failure, arrhythmia, and many others. Heart failure, often called a congestive heart failure ("CHF") or congestive cardiac failure ("CCF"), can occur when the heart is unable to provide sufficient pumping action to distribute blood flow to the body. Treatment of the heart failure can include a surgical intervention (e.g., implantation of various devices (such as pacemakers, ventricular assist devices, etc.), angioplasty, coronary artery bypass graft ("CABG"), heart transplant, and/or other surgical measures), lifestyle changes (such as smoking cessation, light exercise, dietary changes, etc.), medications, and/or any other measures. Heart failure is a common, costly, disabling, and potentially deadly condition.

Increase in fluid and/or blood pressure in the body of the patient can be an important factor in the development of the congestive heart failure disease. Thus, measurement of such pressure can aid in CHF prediction, detection and/or management. However, conventional monitoring systems have a high percentage of false alarms that occur in CHF prediction as such systems are unable to properly correlate fluid accumulation in patient's lungs to blood pressure. Further, such conventional systems are unable to perform an accurate determination of fluid in the pulmonary system of the patient and combine such determination with blood pressure measurement to generate precise prediction of a CHF event.

SUMMARY

In some embodiments, the current subject matter relates to an apparatus for monitoring and/or performing a diagnosis. The apparatus can include a first implantable device for measuring a property of a first tissue in a body and having a housing. The housing can include a first processing circuitry for causing the first implantable device to measure the property of the first tissue using at least one of the following: an RE measurement of the property of the first tissue or an analysis of a signal reflected from the first tissue, wherein the signal is transmitted by the first implantable device toward the first tissue. The apparatus further can include a second implantable device for measuring a property of a second tissue in the body and having a housing. The housing can include a second processing circuitry for causing the second implantable device to measure the property of the second tissue using at least one sensor. The second implantable device can be communicatively coupled to the first implantable device and provides information about the measured property of the second tissue to at least one of the following: the first implantable device and at least one processing device disposed externally to the body.

In some embodiments, the current subject matter can include one or more of the following optional features. The first implantable device can include a power source for powering the first implantable device. The first implantable device can transmit energy to the second implantable device to power the second implantable device. The property of the first tissue is at least one of: a level of hydration of the first tissue, a dielectric property of the first tissue, and an radio frequency ("RF") measurement of the first tissue, and wherein the property of the second tissue can be blood pressure.

In some embodiments, the first implantable device can include an antenna selected from a group consisting of: a dipole antenna, a wire loops antenna, a stent-based antenna, and a printed antenna. The first implantable device can wirelessly communicate with the second implantable device. In some embodiments, the first implantable device can be connected with the second implantable device using a wire.

In some embodiments, the housing of the first implantable device can contain the second implantable device, wherein a power source of the first implantable device powers the second implantable device. In some embodiments, the second implantable device can be selected from a group consisting of pulmonary artery blood pressure sensor and a left atrium pressure sensor.

In some embodiments, the housings of the first and second implantable devices are manufactured from a biocompatible material.

In some embodiments, the second implantable device can reflect at least one signal transmitted by the first implantable device, wherein the first implantable device receives the reflected signal. The second implantable device can modulate the signal prior to reflecting the signal transmitted by the first implantable device.

In some embodiments, the current subject matter can relate to an apparatus for monitoring and/or performing a diagnosis. The apparatus can include an implantable device for measuring a property of a tissue in a body and having a housing. The implantable device can be implanted in a lumen in the body. The housing can include an antenna and a processing circuitry for causing the implantable device to measure the property of the tissue using the antenna. The implantable device can generate a radio frequency signal and determine, based on the generated signal, at least one property of at least one tissue of the lumen, wherein the at least one property includes at least one of the following: a pressure inside the lumen, a dielectric property of at least one tissue in proximity to the lumen, an electro-magnetic property of at least one tissue proximal to the lumen, and a level of hydration of at least one tissue proximal to the lumen.

In some embodiments, the current subject matter can include one or more of the following optional features. The implantable device can be implanted wholly or (partially in a lumen inside the body, wherein implantable device supports at least one interior wall of the lumen. In some embodiments, at least one sensor can be at least one of the following: a RF sensor, a radar, and a dielectrometer. In some embodiments, the antenna can be at least one of the following: a dipole antenna, a wire loops antenna, a stent-based antenna, and a printed antenna. In some embodiments, the lumen can be at least one of the following: a pulmonary artery, a spleen, and a splancnic vessel.

In some embodiments, the implantable device can transmit a signal indicative of the determined property to at least one device located externally to the body.

In some embodiments, the current subject matter relates to an apparatus for monitoring and/or performing a diagnosis. The apparatus can include an antenna for measuring a property of a tissue in a body, the antenna being embedded in a tube disposed in the hod and processing circuitry coupled to the antenna. The circuitry can generate a radio frequency signal and determine, based on the generated signal, at least one property of at least one tissue, wherein the at least one property includes at least one of the following: a dielectric property, an electro-magnetic property, and a level of hydration.

In some embodiments, the tube is a surgical drain tube. In some embodiments, the tube is a catheter. In some embodiments, the tube is a urine catheter. In some embodiments, the tube is an injection line. In some embodiments, the tube is a tracheal tube. In some embodiments, the apparatus is used to measure a peripheral edema. In some embodiments, the apparatus is used to measure a subcutaneous edema. In some embodiments, the apparatus is used to measure an intestinal edema.

In some embodiments, the current subject matter relates to a method for monitoring and/or performing a diagnosis using a system having a first implantable device having a housing including a first processing circuitry, and a second implantable device having a housing including a second processing circuitry, the second implantable device is communicatively coupled to the first implantable device. The method can include measuring, using the first implantable device, a property of a first tissue in the body using at least one of the following: an RE measurement of the property of the first tissue or an analysis of a signal reflected from the first tissue, wherein the signal is transmitted by the first implantable device toward the first tissue, measuring, using the second implantable device, a property of a second tissue in the body with at least one sensor, and providing, using the second implantable device, information about the measured property of the second tissue to at least one of the following: the first implantable device and at least one processing device disposed externally to the body.

In some embodiments, the method can also include transmitting, by the first implantable device, energy to the second implantable device and powering the second implantable device using at least a portion of the transmitted energy.

In some embodiments, the current subject matter relates to a method for monitoring and/or performing a diagnosis using an implantable device for measuring a property of a tissue in a body and having a housing, the implantable device being implanted in a lumen in the body, the housing including an antenna and a processing circuitry for causing the implantable device to measure the property of the tissue using the antenna. The method can include generating a radio frequency signal and determining, based on the generated signal, at least one property of at least one tissue of the lumen, wherein the at least one property includes at least one of the following: a pressure inside the lumen, a dielectric property of at least one tissue proximal to the lumen, an electro-magnetic property of at least one tissue proximal to the lumen, and a level of hydration of at least one tissue proximal to the lumen.

In some embodiments, the method can also include transmitting, using the implantable device, a signal indicative of the determined property to at least one device located externally to the body.

In some embodiments, the current subject matter relates to a method for monitoring and/or performing a diagnosis using an antenna for measuring a property of a tissue in a body and a processing circuitry coupled to the antenna, wherein the antenna being embedded in a tube disposed in the body. The method can include generating a radio frequency signal and determining, based on the generated signal, at least one property of at least one tissue, wherein the at least one property includes at least one of the following: a dielectric property, an electro-magnetic property, and a level of hydration.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE FIGURES

The accompanying drawings, which are incorporated in and constitute a part of this specification, show certain aspects of the subject matter disclosed herein and, together with the description, help explain some of the principles associated with the disclosed embodiments. In the drawings.

DETAILED DESCRIPTION

Figure 1:
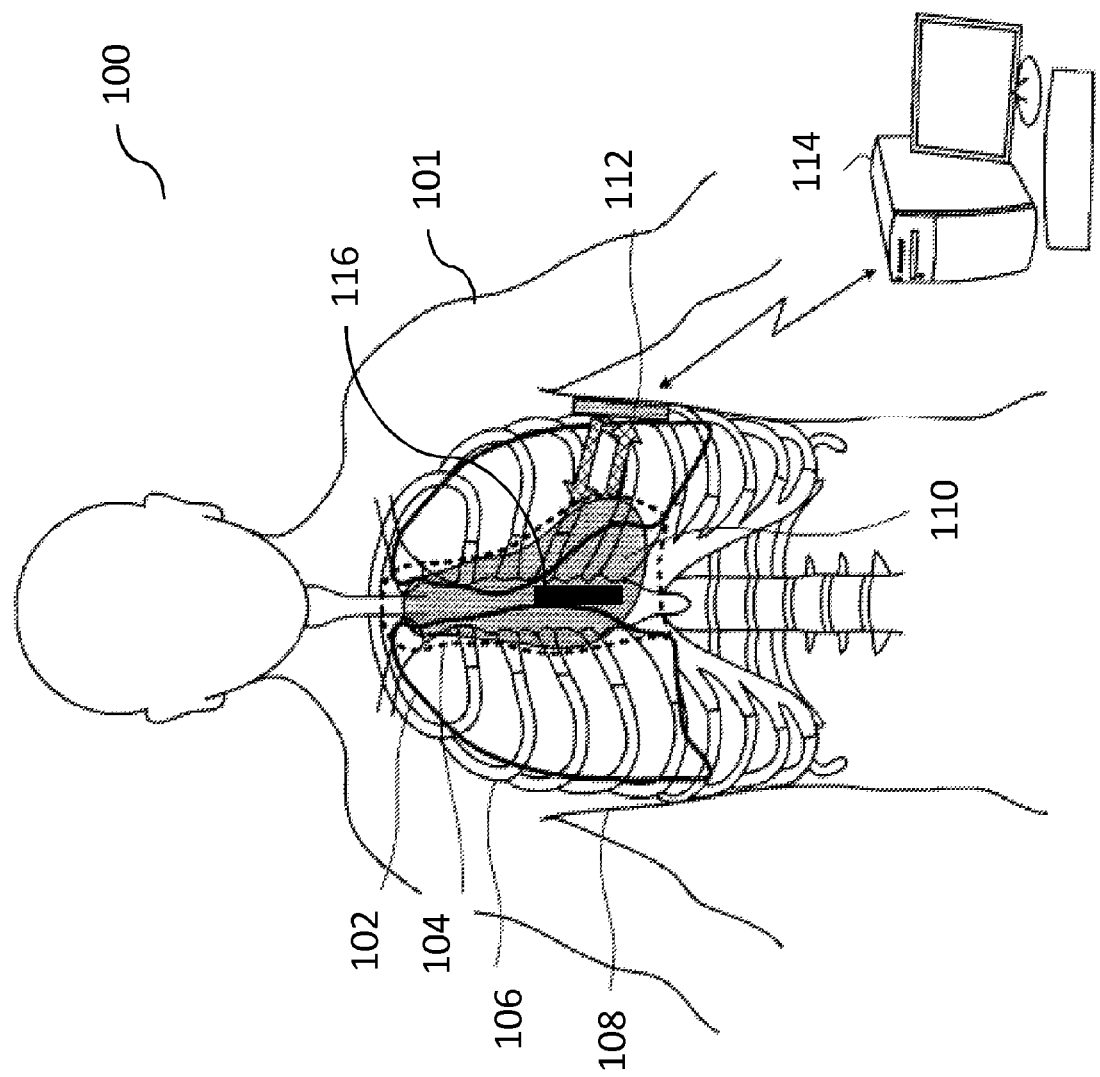
FIG. 1 illustrates an exemplary monitoring system, according to some embodiments of the subject disclosure.

In some embodiments, systems, methods and devices are provided for monitoring and performing a diagnosis of cardiovascular, cardiopulmonary and/or other heart-related systems in the body of the patient. The systems can implement microwave and/or radio-frequency ("RF") monitoring and/or sensing components. Some such exemplary monitoring/diagnostic systems are disclosed in the co-owned/co-pending U.S. patent application Ser. No. 12/759,715, the disclosure of which is incorporated herein by reference in its entirety. The monitoring/diagnostic systems can be used to measure levels of various fluids (e.g., lung fluid level) within the body of the patient, measure pressure of the fluids (e.g., blood pressure), and then correlate such measurements to determine whether a possibility of an acute decompensated heart failure condition (or other condition) exists. In some exemplary embodiments, the current subject matter system can include a combination of RF sensors and/or devices with pulmonary artery blood pressure ("PAP") devices and/or left atrium pressure ("LAP") devices. Further, some embodiments of the current subject matter can incorporate various therapeutic aspects, such as, drug delivery devices, defibrillators, pacing device, etc.

A number of chronic medical conditions can lead to an accumulation of fluid in and around body organs. For example, pulmonary edema can be associated with chronic heart failure and/or other pathologies. As another example, conditions, such as kidney failure and certain inflammatory disorders, can lead to pericardial effusion. Monitoring such fluid levels in the body of the patient over extended periods can be helpful in assessing risk of a particular disease and/or determination of appropriate treatment.

In some embodiments, the current subject matter relates to a monitoring system that can include one or more implantable devices that can be used for measurement and monitoring of tissue characteristics, such as fluid accumulation in and around body organs. The implantable device can include an antenna and associated processing circuitry, which can be contained inside or connected to a sealed case made from a biocompatible material. The device can be implanted within the body of a patient proximal to a target tissue, e.g., the lung of the patient. The antenna can receive RF electromagnetic waves transmitted through the target tissue. The RF waves can be transmitted by the antenna and then reflected back through the target tissue to the device. The reflected RF waves can also be reflected from a reflecting device, such as a dielectrometer, that can be placed in the target tissue or in close proximity to the target tissue (e.g., the antenna and the dielectrometer can be so arranged that the target tissue is placed between the two). The RF waves can also be transmitted from another source to the target tissue. Additionally, the reflected RF waves can be reflected to a receiving device other than the implantable device (e.g., a device that is external to the body of the patient). Alternatively, the implantable device can transmit the reflected RF waves to another device (e.g., a device that is external to the body of the patient). The processing circuitry can process signals that are received by the antenna to derive and output an indication of a characteristic of the target tissue, such as the tissue fluid content.

In some embodiments, the implantable device can be implanted in the thorax, e.g., adjacent to the lung. The processing circuitry can drive the antenna to transmit RF waves through the lung toward the heart of the patient, and to receive waves reflected from the heart and transmitted back through the lung. Alternatively, the waves can be reflected back from a dedicated reflector or another reflective object. In some embodiments, the current subject matter system can include a separate transmitter and receiver components that can be placed at various locations on the target tissue, whereby the transmitter component can transmit waves through the target tissue toward and for receiving by the receiver component. The processing circuitry can process the signals that are received to derive a measure of the fluid content of the lung. The processing circuitry of the implantable device can generate a report containing a fluid level in the lung. The report can be generated on a periodic basis, upon a request from another device (e.g., a device external to the body of the patient). The report can be transmitted by a telemetric link to an external device. It can be used by a physician in tracking the patient's condition and making treatment changes as appropriate.

FIG. 1 illustrates an exemplary monitoring system 100, according to some embodiments of the current subject matter. The system 100 can be used with a patient 101, which can be a human, a mammal, and/or any other subject. The system 100 can include a radio frequency monitoring device 112, a sensor 116, and an external processing system 114. The RF monitoring device 112 can be implanted in the thorax 108 of the patient 101. The sensor 116 can be pulmonary artery blood pressure device that can be implanted in the pulmonary artery of the patient 101). The device 112 can be similar in shape and/or size to an implanted cardiac device ("ICD") and can be implanted below the skin of the patient and adjacent to the ribs. The device 112 can transmit and receive RF electromagnetic waves through target tissue, such as a lung 102, as indicated by arrows in FIG. 1. RF waves can also be transmitted toward the PAP sensor 116 in order to energize the PAP sensor 116. The PAP sensor 116 can be a passive radio-frequency ("RF") device that can absorb and store, using known mechanisms, electromagnetic energy transmitted by the device 112 to energize its circuits. The PAP sensor 116 can determine the pressure inside the pulmonary artery vein and transmit the pressure information back to the device 112, which can transmit this information to the external system 114. Alternatively, the PAP sensor 116 can transmit the pressure information directly to the external system 114.

In some embodiments, the device 112 can be implanted in the axillary region using a minimally-invasive procedure. The waves transmitted by device 112 pass through lung 102 and mediastinum 104, reflect back from heart 110 through lung 102, and are then received and detected by device 112. The device 112 can be implanted in any other location on the body of the patient (such as the infra-mammary or dorsal regions of thorax 108). During implantation process of the device 112, the surgeon (or any other medical professional) can determine an optimal location for device 112 based on the strength of the reflected signal to the device 112. For example, an external antenna (not shown in FIG. 1) can be used for such purposes, whereby the external antenna transmits a signal toward the tissue and receives a reflected signal, based on strength of which the surgeon determines where the implant the device 112.

The device 112 can process the received RF signal to derive an indication of tissue characteristics, such as tissue fluid content. The device 112 can collect these indications over time and transmits the data to the external system 114. This can be accomplished through use of any suitable short-range wireless link. The system 114 can include a general purpose computer, with suitable communication circuits and software. The system 114 can also be configured to communicate, program, and/or provide instructions to the device 112 and/or the device 116 over the wireless link. The system 114 can also provide RF energy to charge/recharge battery of the device 112 and/or device 116 and/or charge/recharge capacitive circuits in the device 116 (in the event the device 116 directly can communicate with the station 114 and is a passive device).

In some embodiments, the device 116 can be a left atrium pressure measurement device that can be implanted in the appropriate section of the heart 110 for measuring the pressure in the left atrium of the heart 110 of the patient 101. Further, the device 116 can be any intra-vascular and/or extra-vascular pressure measurement device that can be implanted in the heart 110 and/or at the heart 110. It can also be a combination of intra- and extra-vascular devices. The device 116 can also be surgically implanted by a surgeon (or any other medical professional).

The implantation of the device 112 and/or 116 can be performed using minimally invasive procedures, such as, using catheterization, an angioplasty, etc., and/or during a surgical procedure (e.g., open heart surgery, etc.).

In some embodiments, synergism with other devices involves includes sharing resources (e.g., power sources, communications, and the like) or anatomical locations.

Figure 2:
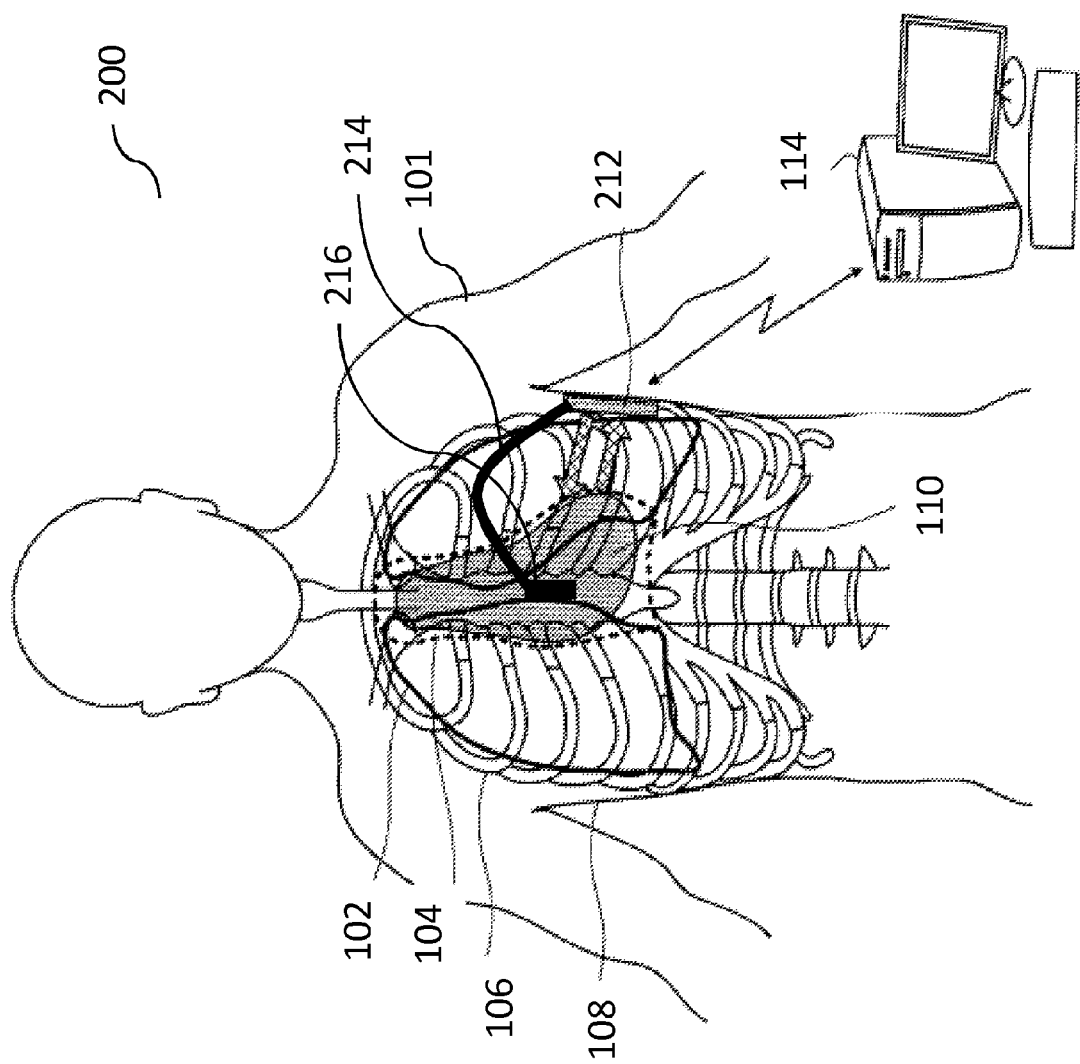
FIG. 2 illustrates another exemplary monitoring system, according to some embodiments of the subject disclosure.

In some embodiments, the devices 112 and 116 can be combined into a single housing, as shown in FIG. 2. As shown in FIG. 2, the system 200 includes a device 212 that can combine the functionalities of the devices 112 and 116 shown in FIG. 1. The device 212 can be connected via a wire 214 to a sensing tip 216. The sensing tip 216 can be implanted in the pulmonary artery of the patient 101 (or in a different anatomical location) and can be used to measure pulmonary artery blood pressure, left atrium blood pressure, and/or any other heart-vessel related pressure. The wire 214 and the tip 216 can be surgically implanted using the techniques discussed above in connection with FIG. 1. The device 212 can communicate with the system 114 in a similar manner as devices 112 and/or 116 shown in FIG. 1. Further, the arrangement shown in FIG. 2 can allow the sensing device and the pressure measurement device to share power, communication and/or the housing. In some embodiments, the housing of the components 112, 116, 212, and 216 can be manufactured from a biocompatible material.

Figure 3:
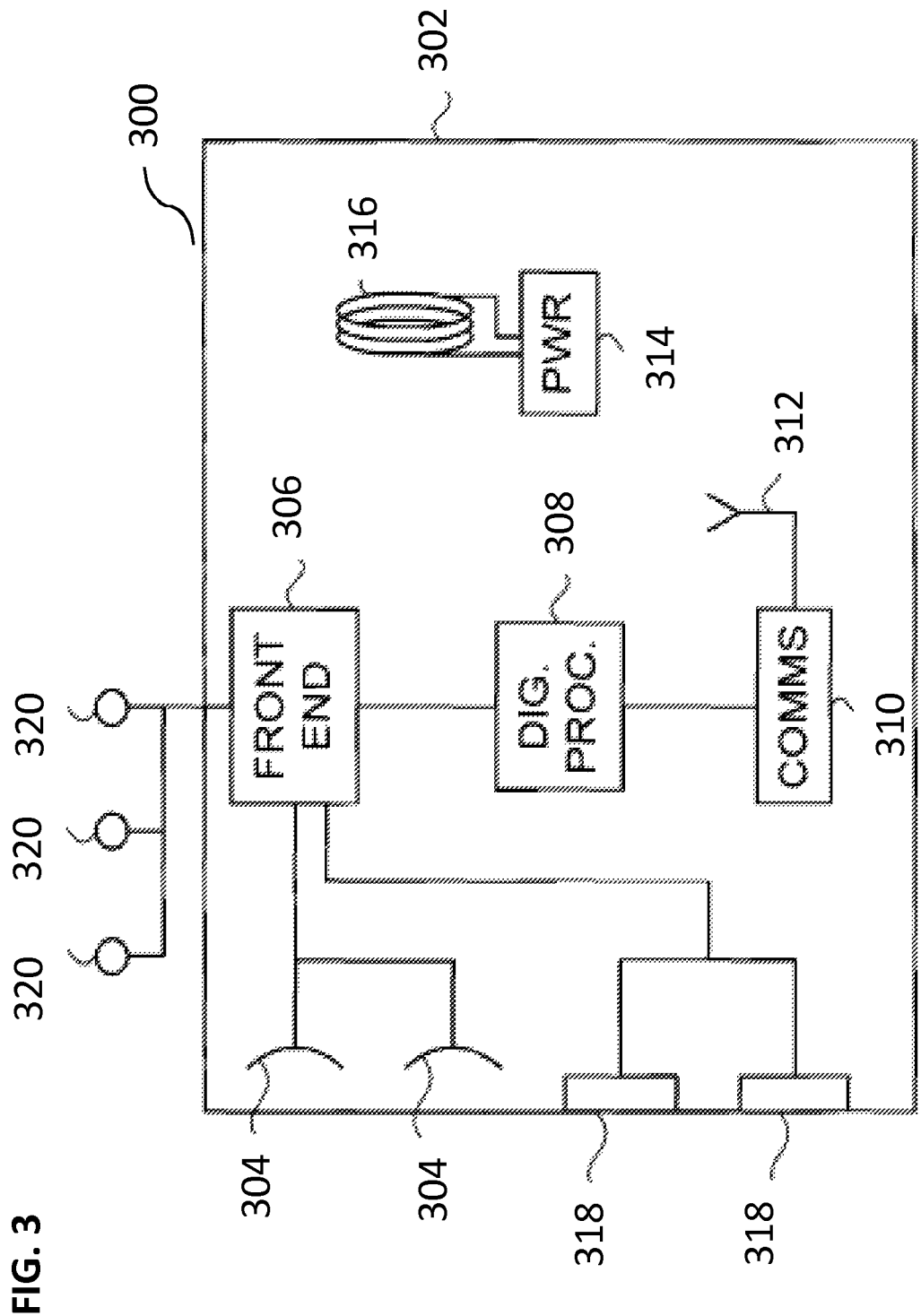
FIG. 3 illustrates an exemplary radio frequency monitoring device, according to some embodiments of the subject disclosure.

FIG. 3 illustrates an exemplary RF monitoring device 300 (similar to the devices 112 and 212 shown in FIGS. 1 and 2, respectively), according to some embodiments of the current subject matter. The device 300 can include a sealed housing 302, which can be manufactured from a suitable biocompatible material, such as titanium and/or stainless steel. The housing 302 can be coated with a tissue-growth inducing material and/or any other material. The device 300 can include at least one antenna 304, a RF front end 306, a processor circuitry (e.g., a digital processor) 308, a communication circuitry 310 along with a transmission antenna 312, a power circuitry 314 along with a power coil 316, a plurality of electrodes 318, and sensors 320.

The housing 302 can include a processing circuitry that can include the RF front end 306, the processor circuitry 308, the communication circuitry 310, and the power circuitry 314. The RF front end 306 can be communicatively coupled to the processor 308, the antenna(s) 304, and the electrodes 318. The RF front end 306 can be also powered by the power circuitry 314. The RF front end 306 can drive the antenna(s) 304 to emit RF waves toward and through the lung(s) of the patient (not shown in FIG. 3). The antenna(s) 304 can be transmit signals toward the lung(s) of the patient and receive signals that are reflected back. In some embodiments, a single antenna 304 can transmit and receive the signals. The RF front end 304 can receive and process reflected signals and can output a digitized indication of the amplitude and phase of the signals to the processor circuitry 308. In some embodiments, the RF front end 304 and/or the processor circuitry 308 can include a plurality of filtering mechanisms to reduce the presence of background noise in the received signals. The RF front end 306 and processor circuitry 308 can apply coherent methods of signal processing to correlate the reflected signals with the transmitted signals (alternatively, non-coherent processing methods can be used).

In some embodiments, the RF front end 306 can generate signals at multiple different frequencies for exciting the antenna(s) 304. In some embodiments, the device 300 can operate in an ultra-wide-band ("UWB") mode, whereby signals can be spread over a wide range of frequencies, such as from approximately 500 MHz to approximately 2.5 GHz and/or any other higher and/or lower frequencies outside this spectrum. UWB transmission and detection techniques are discussed in the co-owned/co-pending International Patent Publication No. WO2011/067623 and U.S. patent application Ser. No. 12/759,715, the disclosures of which are incorporated herein by reference in their entireties. The UWB signal can provide the frequency-domain equivalent of a very short pulse in the time domain and can be used for measuring the range of a reflecting spot in the body with high accuracy. The UWB signal can be transmitted as a short pulse or as a train of narrowband signals that together constitute a wideband signal, or other waveforms can be used in radar pulse compression (such as chirped, stepped-frequency, or phase-coded pulses). Use of these waveforms in making measurements inside the body of the patient is discussed in the co-owned/co-pending International Patent Publication No. WO2011/067623 and U.S. patent application Ser. No. 12/759,715, the disclosures of which are incorporated herein by reference in their entireties.

In some embodiments, the processor circuitry 308 can measure the time delay for RF signal to travel from antenna 304 to the heart via a lung of the patient and back to the antenna 304. The reflected signals from the heart can be identified based on the modulation, typically comprising a cyclical change, of the resulting signal during a heartbeat. The short-term time cyclical variation of the delay from antenna to heart and back can also be used to measure heart movement, while long-term variation can be indicative of changes in the pulmonary fluid level. Additionally or alternatively, electrodes 318, which can be built into the housing 302 and/or mounted externally, can measure an electrocardiogram ("ECG") signal for correlation with the actual heart movement. Further, the processor circuitry 308 can detect modulation of the waves due to respiratory motion.

In some embodiments, the device 300 can include at least one sensor 320. The sensors can be embedded into the housing 302 and/or communicatively coupled to the device 300. The sensors 320 can determine bio-impedance, fluid content, temperature, salinity, and/or motion of the heart, lungs, other organs, and/or entire body and can be used in supplementing determination of the fluid status as provided by RF measurement.

As the RF signals pass through body tissue, such as lung(s) of the patient, the group velocity of the signals can vary as a function of the fluid content of the tissue. For example, the higher the fluid content, the greater the dielectric constant of the tissue will be, and hence, the velocity will be lower. Further, fluid in the lungs can be considered to increase the RF path length of the signals, as defined by the length of time required for the waves to pass through the tissue and back to device 300. The result of this decrease in velocity or increase in RF path length is that the delay of the reflected waves can increase as the fluid content of lung(s) increases. The processor circuitry 308 can determine this delay periodically and/or on command in order to compute an indication of the lung(s) fluid content. The processor circuitry 308 can include a memory (not shown in FIG. 3), which can store the computed values. Further, the processor circuitry can determine other signal characteristics, such as the amplitude of the reflected signals from a transition layer between the ribs and lung(s) of the patient. The amplitude of this reflection can be stronger and differently-shaped in patients suffering from pulmonary edema in comparison to healthier patients. The signal amplitude and shape can be fitted parametrically to a stratified model of the various tissues traversed by the RF waves, wherein the fit parameters include the fluid content.

In some embodiments, the processor circuitry 308 can determine other parameters relating to tissue characteristics, such as the volume, shape, physical properties, locations and/or movement of structures in the path of the RF signals within the body of the patient. For example, the RF signals and signal processing carried out in RF front end 306 and processor circuitry 308 can be adjusted to measure pericardial fluid content within the mediastinum (not shown in FIG. 3). The antenna(s) 304 can be driven in a multi-static configuration to measure the electromagnetic properties of different sub-volumes within thorax (not shown in FIG. 3), and thus, provide data that can be spatially resolved in two or three dimensions. Such multi-static techniques (using extracorporeal antennas) are discussed the co-owned/co-pending International Patent Publication No. WO2011/067623 and U.S. patent application Ser. No. 12/759,715, which also discus digital signal processing methods that can be used to determine the complex dielectric constants for the individual sub-volumes.

The device 300 also includes the communication interface 310, which can transmit and receive data to and from external system 114 (not shown in FIG. 3, but is illustrated in FIG. 1) via the communication antenna 312. The transmitted data can include indications of tissue characteristics that have been computed over time and stored by the processor circuitry 308. These indications can include statistical parameters determined by the processor circuitry 308 over the tissue measurement results, such as time trend parameters of the measured fluid level. The indications of tissue characteristics can include raw data collected from RF front end 306. The communication interface 310 can transmit data either intermittently or continuously as the data is being measured. The communication interface 310 can communicate with other implanted diagnostic and/or therapeutic devices, such as an intravascular pressure sensor or an ICD, or with non-invasive monitoring devices, such as a bio-impedance measurement device.

The communication interface 310 can also communicate data that it receives from the device 116 (shown in FIG. 1), where the data can include measurements of pulmonary artery pressure, left atrium pressure, and/or any other data that may be related to the operation of the heart of the patient.

In some embodiments, the processor circuitry 308 can combine and/or process data related to reflected signals as received by the antenna(s) 304, the sensors 320, the electrodes 318, and/or pressure data that is received from the device 112 (shown in FIG. 1 (or device 212 shown in FIG. 2)). The combined and/or processed data can be supplied to the external system 114 (shown in FIG. 1). Further, based on the signals received from the above components, the processor circuitry 308 can also generate an alarm signal for sending to the external system 114 (or any other system) that can be indicative of a specific patient condition, e.g., CHF. The signal can be generated based on the signals that are received from the above components (e.g., the antenna(s) 304, the sensors 320, the electrodes 318, and/or pressure data that is received from the device 112) exceeding various predetermined thresholds. The processor circuitry 308 can be programmed to compare received data against certain pre-programmed thresholds and upon determining that one or more of them is exceeded, may choose to generate an alarm. The processor circuitry 308 can be also programmed to disregard conditions where one threshold is exceeded while the others are not (e.g., an elevated blood pressure (beyond preprogrammed thresholds) in combination with normal (as preprogrammed) fluid levels in the lung(s) of the patient can be ignored as not indicative of a particular condition)).

In some embodiments, the device 300 can be powered by the power source 314, which can supply operating power to the circuits of device 300. The power source 314 can include an energy storage component, such as a single-use or rechargeable battery. In the case of a rechargeable storage component, the power source 314 can be coupled to the power antenna 316 that can receive RF power from a suitable power transmission antenna (not shown in FIG. 3) that can be disposed outside the housing 302. In some embodiments, the antenna(s) 304 can receive RF power, instead of and/or in addition to the power antenna 316. The power transmission antenna 316 can include a coil, which can be positioned outside the thorax in the proximity to the device 300 and can provide power to the antenna 316 by magnetic induction. The power transmission coil can be placed under a bed on which the patient can be positioned and/or it may be worn by the patient. The power source 314 can rectify the received power in order to charge its energy storage component.

In some embodiments, the current subject matter system can also include an intra-vascular dielectrometer device that can be implanted in a blood vessel for the purposes of measuring dielectric properties of the tissue surrounding the blood vessel. In some embodiments, the intra-vascular dielectrometer device can also measure the pressure inside the blood vessel. The intra-vascular dielectrometer device can be implanted in any vessel, lung, and/or any other organ within the body of the patient. The device can be implanted using any known surgical methodologies (e.g., catheterization, during open heart procedure, etc.)

Figure 4:
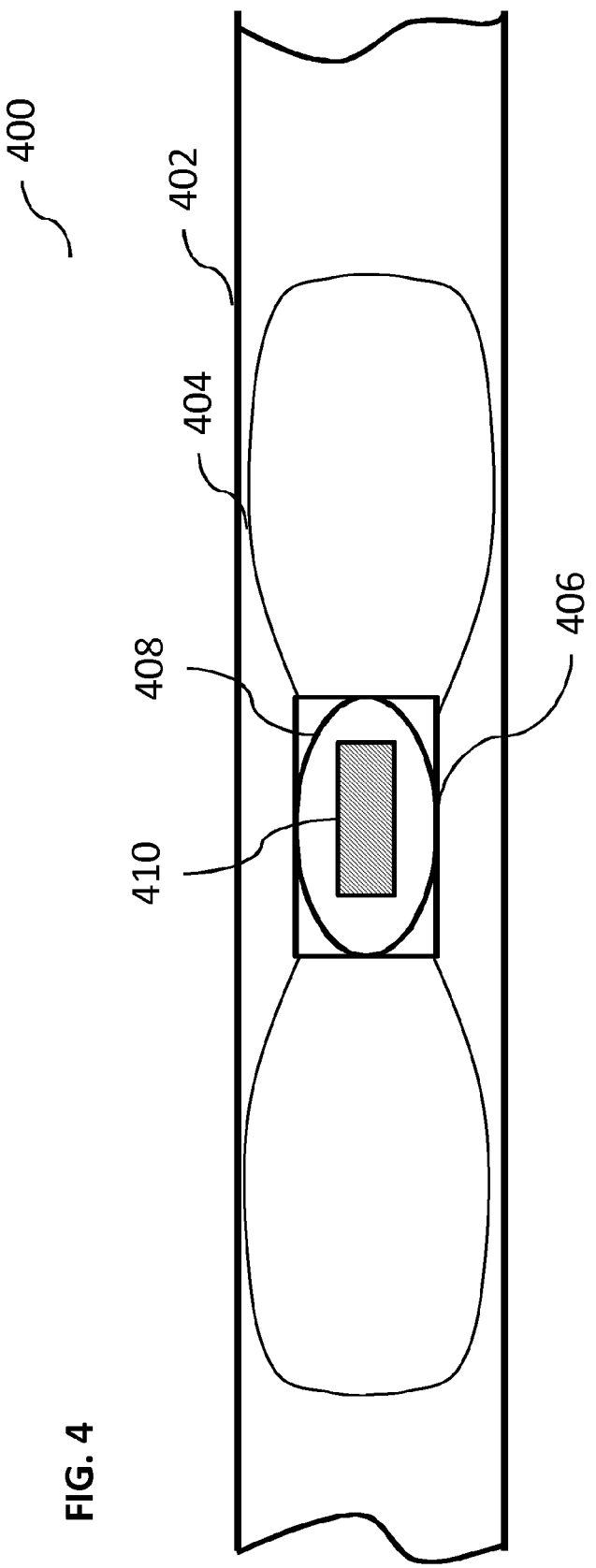
FIG. 4 is a block diagram of an exemplary embodiment of an intra-vascular dielectrometer device that can be implanted inside a blood vessel, according to some embodiments of the subject disclosure.

FIG. 4 is a block diagram of an exemplary embodiment of an intra-vascular dielectrometer device 400 that can be implanted inside a blood vessel 402, according to some embodiments of the current subject matter. The device 400 can include an antenna 404, a housing 406, an RF transmit/receive unit 408 (which can be similar to the RF front end 306 shown in FIG. 3) and integrated circuit electronics 410. In some embodiments, the device 400 can also include an internal power source (not shown in FIG. 4) and/or it can operate without an internal power source and instead be recharged/charged externally using a RF electromagnetic energy that can be transmitted to it using an external device (such as device 300 shown in FIG. 3 and/or external system 114, as shown in FIG. 1). The energy can be received using the antenna 404 and processed by the RF transmit/receive unit 408, whereby the received energy can be stored by an internal conventional capacitance circuit (not shown in FIG. 4) disposed within the integrated circuit electronics 410. Once the sufficient amount of energy is accumulated by the capacitance circuit, the device 400 can trigger operation of the RF transmit/receive unit 408. The unit 408 can determine electro-magnetic properties of the surrounding tissues based on the signal reflections that are received by the antenna 404. The antenna 404 can transmit a continuous waveform ("CW") and/or an UWB pulse toward surrounding tissues and receive reflected signals from the tissues. The received reflected signals can be processed by the RF transmit/receive unit 408 and communicated to the electronics 410, which can determine the properties of reflection from the surrounding tissues. Any change in the tissue's properties (dielectric and/or conductivity) due to fluid accumulation, dehydration, and/or any other condition can change the amplitude and phase of the reflected signals. The device 400 can transmit a signal indicative of this change to an external receiver (e.g., the device 300 (shown in FIG. 3), the external system 114 (shown in FIG. 1), and/or any other device) for the purposes of post processing. Such post-processing can involve analysis of the signals that can be received from the devices that may be implanted in the body of the patient (e.g., device 300, device 116, etc.).

Figure 5A:
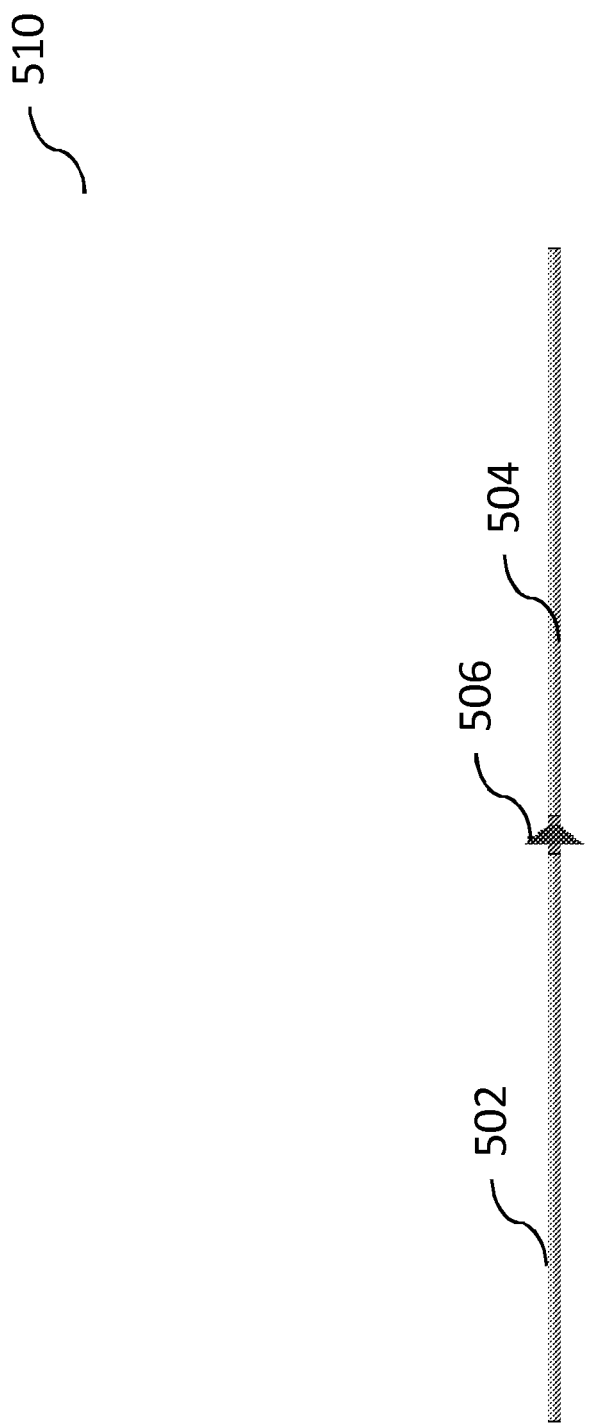
FIGS. 5a-d illustrate exemplary embodiments of antennas that can be used with the monitoring systems shown in FIGS. 1 and 2, according to some embodiments of the subject disclosure.
Figure 5B:
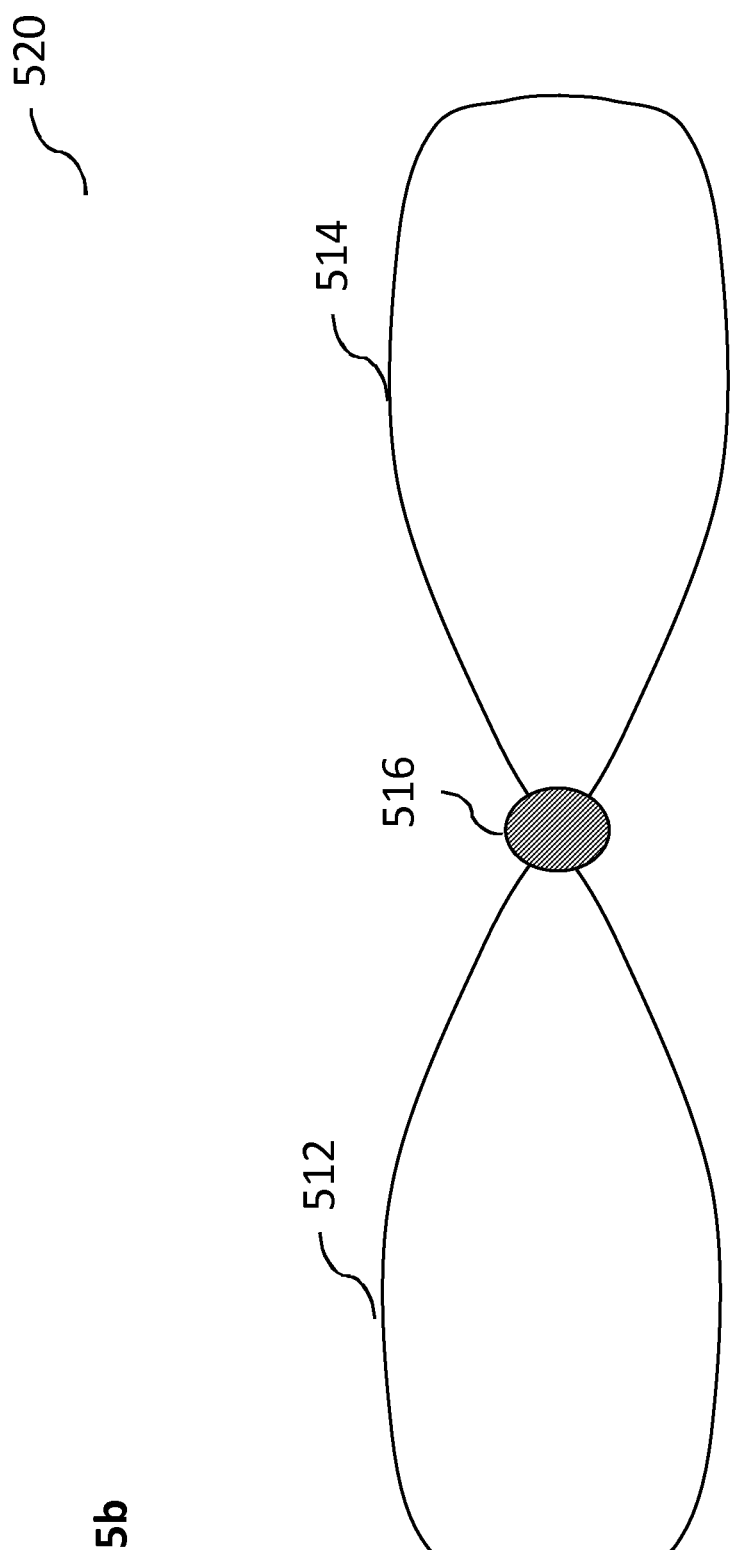
Figure 5C:
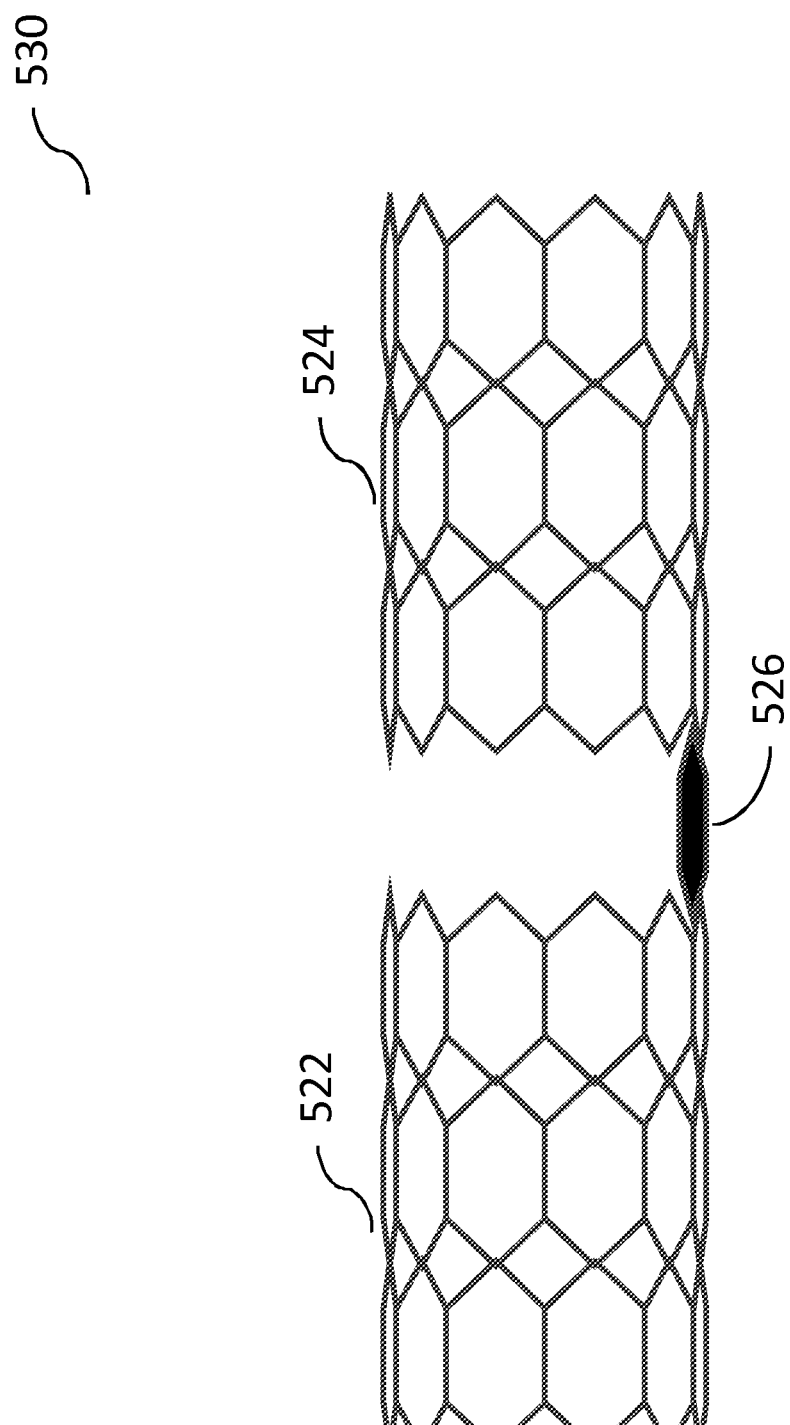
Figure 5D:
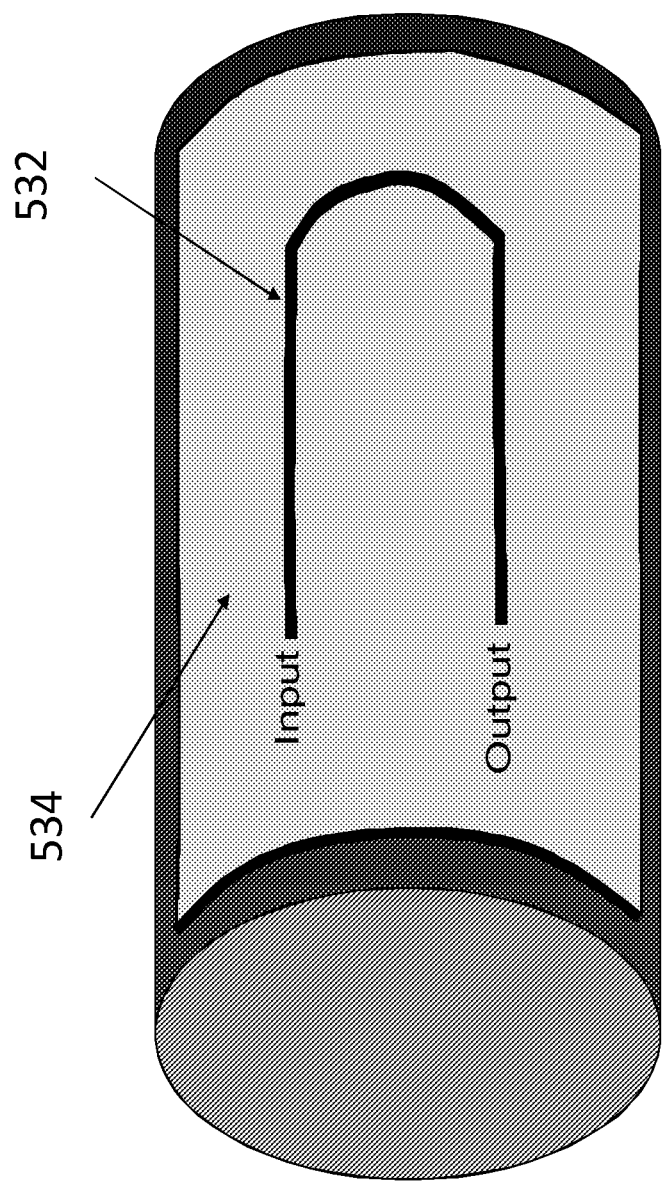

FIGS. 5a-d illustrates various exemplary antennas that can be used in connection with device 400. The antenna can be a dipole antenna 510 (as shown in FIG. 5a), a wire loops antenna 520 (as shown in FIG. 5b), a stent-based antenna 530 (as shown in FIG. 5c), whereby the stent grid serves as the radiator, and/or a printed antenna 540 (as shown in FIG. 5d) that can include an internal ground plane to reduce effect of fluid inside a lumen.

As shown in FIG. 5a, the dipole antenna 510 can include two wires 502 and 504 can be coupled to an electronics component 506. The electronics component 506 can be included in the housing 406 (as shown in FIG. 4).

The wire loops antenna 520 (shown in FIG. 5b) can include metallic structures 512 and 514 that can be coupled to the electronics component 516 that can be included in the housing 406 (as shown in FIG. 4). The structures 512 and 514 can both support the device 400 in the vessel and serve as the antenna.

The stent-based antenna 530 (shown in FIG. 5c) can include two stent structures 522 and 524 coupled to an electronics component 526 that can be included in the housing 406 (as shown in FIG. 4). The structures 522 and 524 can similarly support device 400 in the vessel and serve as the antenna.

The printed antenna 540 (shown in FIG. 5d) can include a microstrip 532 printed on a flexible printed circuit board ("PCB") 534 with a ground plane inside and a conducting line outside.

In some embodiments, the signals that can be received by the antenna in the device 400 can be indicative of at least one of the following: antenna resonance frequency, amplitude of the response at one or more frequencies, and/or phase of the response at one or more frequencies. Further, tracking of phase and/or amplitude of the response signal can be measured at the antenna's resonance frequency range and/or outside of it.

Referring back to FIG. 4, the antenna 404 in the device 400 can serve as an induction antenna for transferring energy into the electronics 410. It can also be used for communication to an external system, such as device 300 and/or external system 114.

In some embodiments, different types of antennas can be used. For example, the antenna/probe can include a resonating structure facing an exterior of the vessel with a ground plane separating it from the blood inside the vessel. Other antenna arrangements can be possible.

In some embodiments, the electronic circuitry 410 of the device 400 can be surrounded by the RFID-like coil 408 that can be used for energy transfer and/or communication. The electronic circuitry 410 can be coated, potted, and/or encapsulated inside a miniature hermetic casing.

In some embodiments, the device 400 can include a functionality of an intra-vascular pulmonary artery pressure sensor (similar to the device 116 shown in FIG. 1) by having a small pressure sensing element integrated into it. In this case, the device 400's electronic circuitry 410 can include various additional components and/or share/use existing components of the circuitry 410 that may be necessary for operation of such sensor (e.g., shared processing, power, communication, mechanical encasement, and the like).

Figure 6:
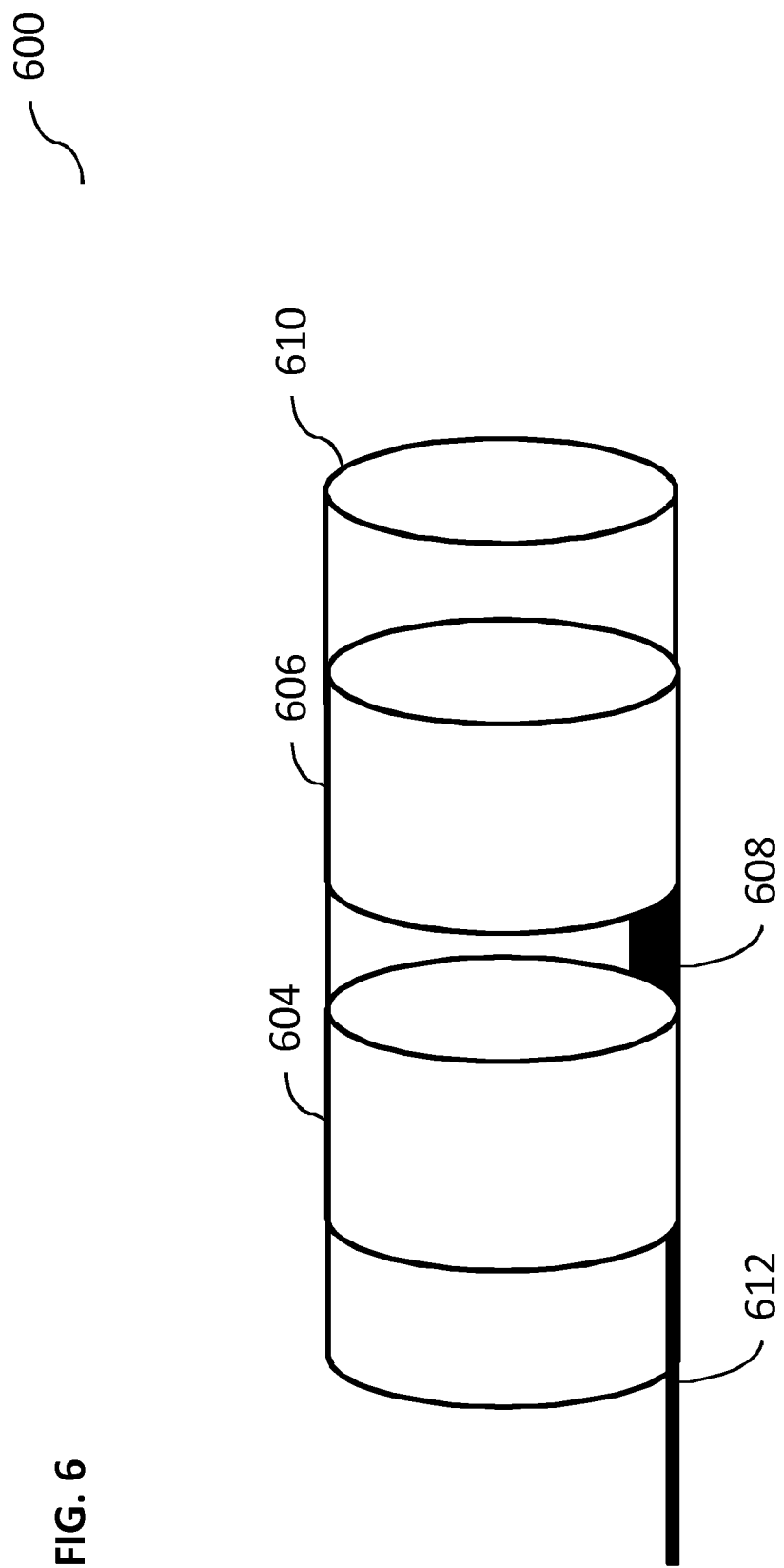
FIG. 6 illustrates an exemplary device that can be embedded in a surgical drain tube, according to some embodiments of the subject disclosure.

In some embodiments, the device 400 can be embedded in a tube. This can be useful for measuring inflammation of tissue, hematomas, and/or any other properties of tissue to assess post-operative healing. FIG. 6 illustrates an exemplary device 600 that can be embedded in a surgical drain tube, according to some embodiments of the current subject matter. The device 600 can be embedded in a tube 610 and can include dipole conducting cylinders 604 and 606. The cylinders 604 and 606 can be coupled using electronics circuitry 608, which is similar to the antenna embodiments discussed above in connection with FIGS. 5a-d. The device can also include a microstrip line 612 for connecting the device 600 to various components. The device 600 can use the dipole antenna as the resonating structure; however, it can be appreciated that other structures can be used. In some embodiments, coaxial and/or three-layer microstrip line leading to the antenna can include a thin profile, and preferably, good isolation to provide sensitive measurement. The microstrip line can be used as a dielectrometer. It can change its electrical properties (e.g., phase, amplitude, resonance frequency, and/or any other properties) based on dielectric properties of the tissue surrounding the microstrip line. In some implementations, the device 600 can include at least one antenna and/or an RF structure for the dielectrometer that can be are printed and/or embedded in the tube 610 and the electronics circuitry 608 can be disposed outside the body of the patient, whereby the microstrip line 612 (and/or a coaxial line, and/or any other connector) can serve as a connection conduit between at least one antenna/RF structure to the electronics circuitry 608. As such, the device 600 can be entirely and/or partially disposed within the tube 600 and/or outside the patient. In some implementations, the tube can be entirely and/or partially disposed internally and/or externally to the body of the patient. The tube can include a surgical drain tube, a catheter, a urine catheter, an injection line, and a tracheal tube. The surgical drain tube can be used during post-surgery. The device 600 placed in the surgical tube (whether entirely or partially) can be used to measure edemas, hematomas, and fluid condition in the tissue surrounding the drain to monitor the healing process and decide when to remove drain. The device 600 that can be used in connection with the urine catheter can include an antenna at the tip of the catheter that can be disposed inside the bladder of the patient. A radar sensor of the device can then measure an echo from the bladder wall to estimate an amount of fluid that can be present in the bladder. The device 600 that can be used in connection with the injection line can be used to detect extravasation. Here, a small antenna disposed in the injection line can detect fluid pockets near the injection line and generate an alarm when extravasation is detected. The device 600 that can be used with the tracheal tube can assist during tube insertion, whereby a dielectrometer on the tracheal tube tip can assist a medical professional in ascertaining whether or not the tube is being or has been inserted properly. In some embodiments, the device 600 can be used to check for a peripheral edema, which is an effective indicator for sepsis and/or other post-operative complications. In this case, a needle with an antenna can be inserted into a muscle tissue and hydration of the tissue can be measured. Here, a rod-like structure instead of a tube can be used to perform the insertion. Additionally, the device 600 can be inserted subcutaneously to measure subcutaneous edema. Further, the device 600 can be used to measure intestinal edema using an RF sensor on a feeding tube (e.g., NG-tube and/or any other tube). In this case, a deep feeding tube can be inserted into the small intestines of the patient and fluid content in the intestine and in the surrounding tissue can be measured. Other exemplary implementations and/or uses of the device 600 are possible.

In some embodiments, the current subject matter can include an implantable monitoring and/or diagnostic apparatus. The device can include an implantable case, an antenna that receives RF waves propagated through proximal target tissue, a processing circuitry configured to derive indication of a characteristic of one or more vital signs of a patient. It can also include at least one the following: a RF propagation reflector, an implantable RF reflector, which may be part of the implantable apparatus, communication means configured for communication with another implanted device, and an implanted device configured to pace heart responsively to circuitry.

In some embodiments, the current subject matter can include an implantable monitoring and/or diagnostic apparatus. The apparatus can include an implantable RF reflector and one or more means configured to transmit RF waves towards a reflector and can be configured for at least one of receiving RF reflections and measuring an indication characteristic of target tissue.

In some embodiments, the current subject matter can include an implantable monitoring and/or diagnostic apparatus. The apparatus can include an implantable case, an implantable dielectrometric probe with at least first and second conductors, circuitry means configured to apply RF and optionally at least one of sensing returned RF and measuring a dielectric property of target tissue, and at least one of the following: communication means configured to communicate with at least one other implanted device, and one or more additional implanted sensors, which may be connected to the case.

Figure 7:
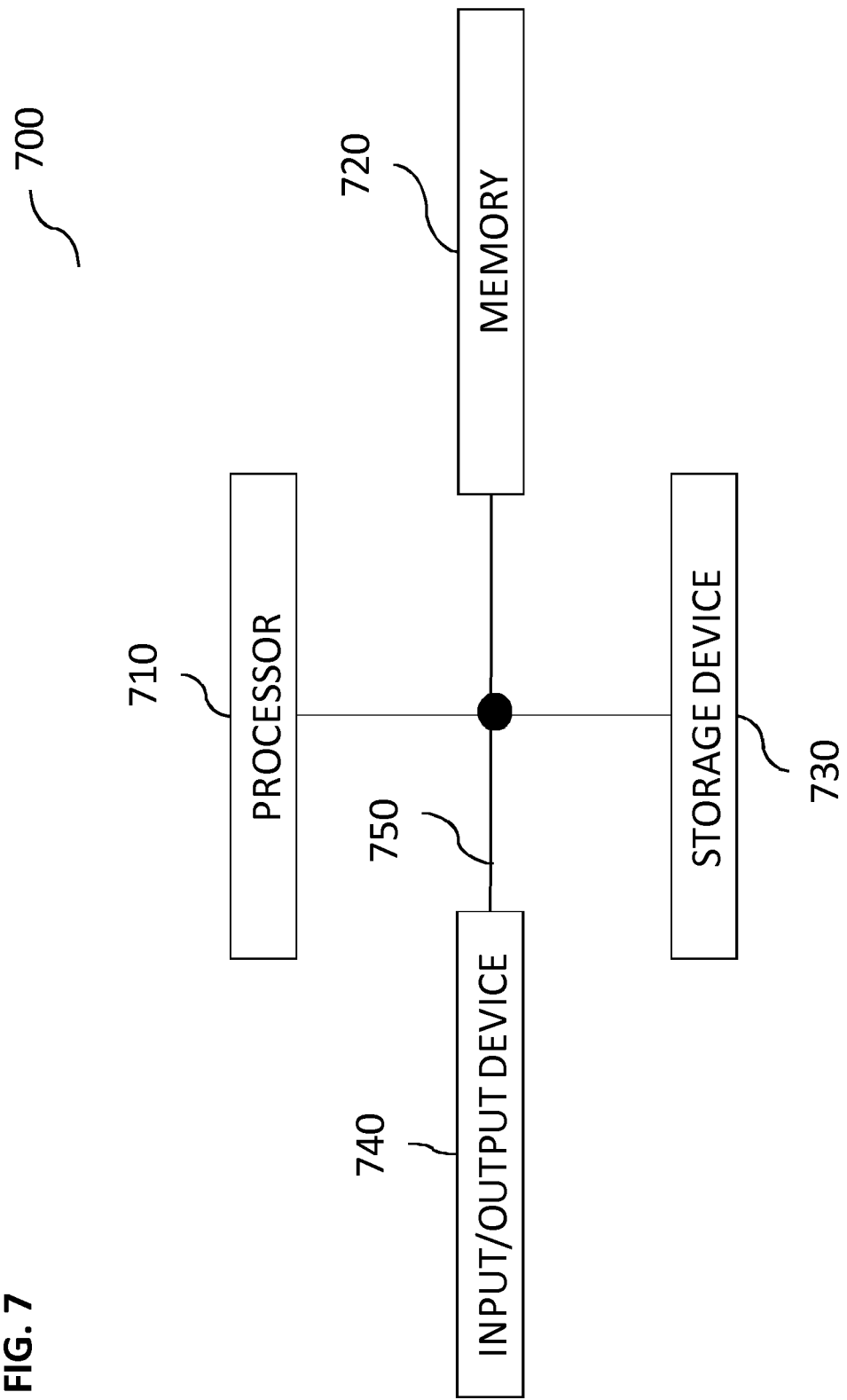
FIG. 7 illustrates an exemplary processing system, according to some embodiments of the subject disclosure.

In some embodiments, some and/or all processing circuitry of the current subject matter can be configured to be implemented in a system 700, as shown in FIG. 7. The system 700 can include a processor 710, a memory 720, a storage device 730, and an input/output device 740. Each of the components 710, 720, 730 and 740 can be interconnected using a system bus 750. The processor 710 can be configured to process instructions for execution within the system 700. In some embodiments, the processor 710 can be a single-threaded processor. In alternate embodiments, the processor 710 can be a multi-threaded processor. The processor 710 can be further configured to process instructions stored in the memory 720 or on the storage device 730, including receiving or sending information through the input/output device 740. The memory 720 can store information within the system 700. In some embodiments, the memory 720 can be a computer-readable medium. In alternate embodiments, the memory 720 can be a volatile memory unit. In yet some embodiments, the memory 720 can be a non-volatile memory unit. The storage device 730 can be capable of providing mass storage for the system 700. In some embodiments, the storage device 730 can be a computer-readable medium. In alternate embodiments, the storage device 730 can be a hard disk device, an optical disk device, a tape device, non-volatile solid state memory, or any other type of storage device. The input/output device 740 can be configured to provide input/output operations for the system 700. In some embodiments, the input/output device 740 can include a keyboard and/or pointing device. In alternate embodiments, the input/output device 740 can include a display unit for displaying graphical user interfaces.

In some embodiments, the current subject matter can be directed to an apparatus for monitoring and/or performing a diagnosis. The apparatus can include a first implantable device (e.g., a device 112, as shown in FIG. 1) for measuring a property (e.g., a level of hydration of the tissue, a dielectric property of the tissue, and a radio frequency ("RF") measurement of the tissue, etc.), of a first tissue in a body and having a housing (e.g., housing 302, as shown in FIG. 3). The housing can include a first processing circuitry (e.g., processing circuitry 308, as shown in FIG. 3) for causing the first implantable device to measure the property of the first tissue using at least one of the following: an RF measurement of the property of the first tissue or an analysis of a signal reflected from the first tissue, wherein the signal is transmitted by the first implantable device toward the first tissue. The apparatus can also include a second implantable device (e.g., device 116, as shown in FIG. 1) for measuring a property (e.g., blood pressure) of a second tissue in the body and a having a housing. The housing of the second implantable device can include a second processing circuitry for causing the second implantable device to measure the property of the second tissue using at least one sensor. The second implantable device can be communicatively coupled to the first implantable device. The second implantable device can provide information about the measured property of the second tissue to at least one of the following: the first implantable device and at least one processing device (e.g., device 114 as shown in FIG. 1) disposed externally to the body. The information that devices can generate can be indicative of a CHF decompensation and/or any other condition.

In some embodiments, the current subject matter can include one or more of the following optional features.

In some embodiments, the first implantable device can include a power source (e.g., power source 314, as shown in FIG. 3) for powering the first implantable device. In some embodiments, the first implantable device can transmit energy to the second implantable device to power the second implantable device.

In some embodiments, the property of the second tissue can be blood pressure and the property of the first tissue can be at least one of the following: a level of hydration of the first tissue, a dielectric property of the first tissue, and an radio frequency ("RF") measurement of the first tissue, and wherein the property of the second tissue is blood pressure.

In some embodiments, the first implantable device can include an antenna that can be at least one of the following:

a dipole antenna, a wire loops antenna, a stent-based antenna, and a printed antenna.

In some embodiments, the first implantable device can wirelessly communicate with the second implantable device.

In some embodiments, the first implantable device can be connected with the second implantable device using a wire.

In some embodiments, the housing of the first implantable device can include the second implantable device. The power source of the first implantable device can power the second implantable device.

In some embodiments, the second implantable device can be at least one of the following: pulmonary artery blood pressure sensor, a left atrium pressure sensor, and/or any other sensors. Exemplary sensors are discussed in the co-owned/co-pending International Patent Publication No. WO2011/067623 and U.S. patent application Ser. No. 12/759,715.

In some embodiments, the housings of the first and second implantable devices can be manufactured from a biocompatible material, including, for example, stainless steel, titanium, nylon, polytetrafluoroethylene ("PTFE"), and/or any other materials.

In some embodiments, the first implantable device can be implanted in a lumen inside the body. The first implantable device can support at least one interior wall of the lumen. The lumen can include at least one of the following: a pulmonary artery, a spleen, and a splancnic vessel.

In some embodiments, the first implantable device can generate at least one of the following signals: a continuous wave signal and an ultra-wideband pulse signal toward at least one tissue of the lumen. The first implantable device can determine, based on the generated signal, at least one property of at least one tissue of the lumen. The property can include at least one of the following: a pressure inside the lumen, a dielectric property of at least one tissue of the lumen, an electro-magnetic property of at least one tissue of the lumen, and a level of fluid inside the lumen. The first implantable device can transmit a signal indicative of the determined property to at least one device located externally to the body.

In some embodiments, the first implantable device either wholly or partially (e.g., just an antenna part and/or the RF structure of the device) can be embedded in a tube disposed either within the body or externally to the body, the first implantable device measures level of fluid inside the tube. The tube can be a surgical drain tube. The tube can also be a catheter. The tube can also be a urine catheter. The tube can also be an injection line. The tube can also be a tracheal tube. Further, the first implantable device can be used to measure edema (either peripheral edema, subcutaneous edema, intestinal edema, etc.)

In some embodiments, the second implantable device can reflect at least one signal transmitted by the first implantable device. The first implantable device can receive the reflected signal. The second implantable device can also modulate the signal prior to reflecting the signal transmitted by the first implantable device.

In some embodiments, the current subject matter relates to an apparatus for monitoring and/or performing a diagnosis. The apparatus can include an implantable device (e.g., device 400 as shown in FIG. 4) for measuring a property of a tissue in a body and having a housing. The implantable device can be implanted in a lumen in the body. The housing (e.g., housing 406 as shown in FIG. 4) can include a processing circuitry (e.g., circuitry 410 shown in FIG. 4) for causing the implantable device to measure the property of the tissue using at least one sensor. The device can generate at least one of the following signals: a continuous wave signal and an ultra-wideband pulse signal, and determine, based on the generated signal, at least one property of at least one tissue of the lumen. The property can include at least one of the following: a pressure inside the lumen, a dielectric property of at least one tissue of the lumen, an electro-magnetic property of at least one tissue of the lumen, and a level of hydration inside the lumen.

In some embodiments, the sensor can be at least one of the following: a RF sensor, a radar, a dielectrometer, a pressure sensor, a pulmonary artery blood pressure sensor and a left atrium pressure sensor.

In some embodiments, the implantable device can include at least one antenna (e.g., antenna 404 as shown in FIG. 4) that can be communicatively coupled to the processing circuitry. The antenna can be at least one of the following: a dipole antenna, a wire loops antenna, a stent-based antenna, and a printed antenna (as shown in FIGS. 5*a-d*).

In some embodiments, the lumen can be at least one of the following: a pulmonary artery, a spleen, and a splancnic vessel.

In some embodiments, the implantable device can transmit a signal indicative of the determined property to at least one device located externally to the body.

In some embodiments, the antenna of the device can be embedded in a tube disposed either within the body or externally to the body, the device measures level of hydration or fluid volume in the tissue surrounding the tube. The tube can include at least one of the following: a surgical drain tube, a catheter, a urine catheter, an injection line, and a tracheal tube.

Figure 8:
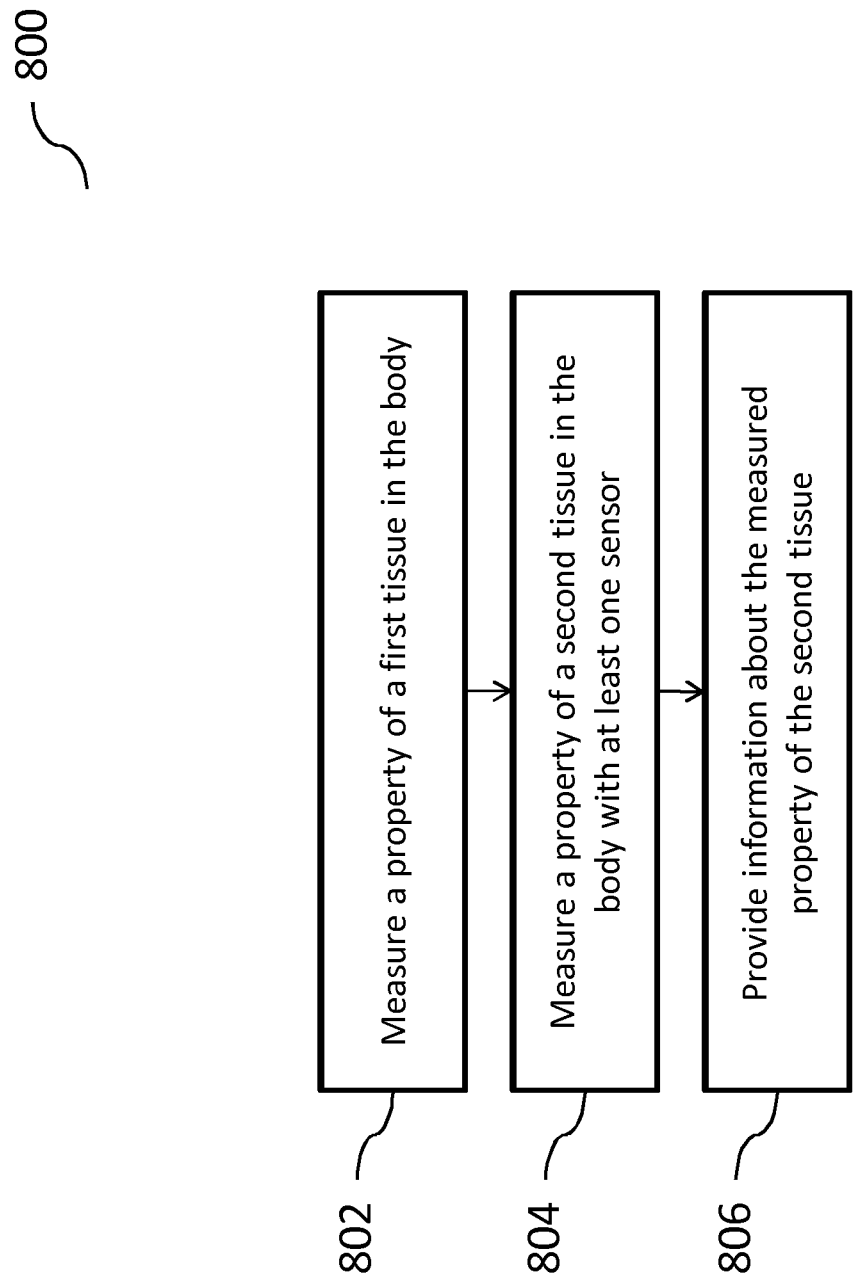
FIG. 8 illustrates an exemplary method, according to some embodiments of the subject disclosure.

In some embodiments, the current subject matter relates to a method 800 for performing monitoring and/or diagnosis using the above-referenced system, as shown in FIG. 8. At 802, the first implantable device can measure a property of a first tissue in the body using at least one of the following: an RF measurement of the property of the first tissue or an analysis of a signal reflected from the first tissue, wherein the signal is transmitted by the first implantable device toward the first tissue. At 804, the second implantable device can measure a property of a second tissue in the body with at least one sensor. At 806, the second implantable device can provide the information about the measured property of the second tissue to at least one of the following: the first implantable device and at least one processing device disposed externally to the body.

Figure 9:
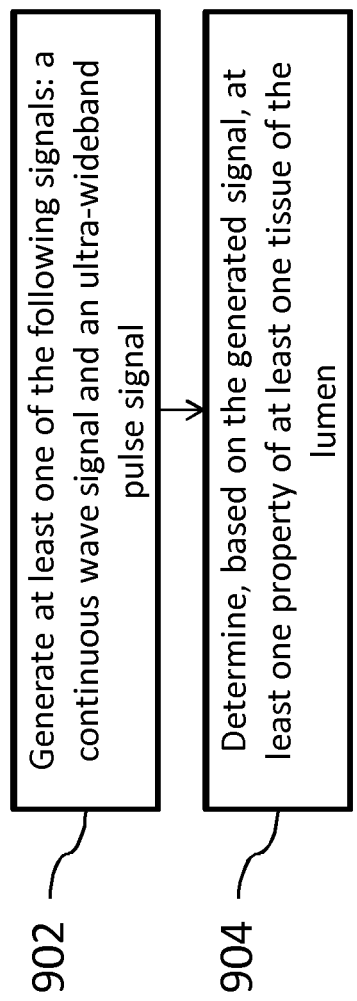
FIG. 9 illustrates an exemplary method for monitoring and/or performing a diagnosis, according to some embodiments of the current subject matter.

FIG. 9 is a flowchart illustrating an exemplary method 900 for monitoring and/or performing a diagnosis, according to some embodiments of the current subject matter. The method can be performed using an implantable device (e.g., device 400 shown in FIG. 4) for measuring a property of a tissue in a body and having a housing. The implantable device can be implanted in a lumen in the body. The housing can include a processing circuitry for causing the implantable device to measure the property of the tissue using at least one sensor. At 902, at least one of the following signals: a continuous wave signal and an ultra-wideband pulse signal can be generated by the device. At 904, based on the generated signal, at least one property of at least one tissue of the lumen can be determined. The property can include at least one of the following: a pressure inside the lumen, a dielectric property of at least one tissue of the lumen, an electro-magnetic property of at least one tissue of the lumen, and a level of hydration inside the lumen.

The subject matter described herein may be embodied in systems, apparatus, methods, and/or articles depending on the desired configuration. In particular, various embodiments of the subject matter described herein may be realized in digital electronic circuitry, integrated circuitry, specially designed ASICs (application specific integrated circuits), computer hardware, firmware, software, and/or combinations thereof. These various embodiments may include embodiment in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal.

Similarly, systems are also described herein that may include a processor and a memory coupled to the processor. The memory may include one or more programs that cause the processor to perform one or more of the operations described herein.

Although a few variations have been described in detail above, other modifications or additions are possible. In particular, further features and/or variations may be provided in addition to those set forth herein. For example, the embodiments described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. Other embodiments may be within the scope of the following claims.

The systems and methods disclosed herein can be embodied in various forms including, for example, a data processor, such as a computer that also includes a database, digital electronic circuitry, firmware, software, or in combinations of them. Moreover, the above-noted features and other aspects and principles of the present disclosed embodiments can be implemented in various environments. Such environments and related applications can be specially constructed for performing the various processes and operations according to the disclosed embodiments or they can include a general-purpose computer or computing platform selectively activated or reconfigured by code to provide the necessary functionality. The processes disclosed herein are not inherently related to any particular computer, network, architecture, environment, or other apparatus, and can be implemented by a suitable combination of hardware, software, and/or firmware. For example, various general-purpose machines can be used with programs written in accordance with teachings of the disclosed embodiments, or it can be more convenient to construct a specialized apparatus or system to perform the required methods and techniques.

As used herein, the term "user" can refer to any entity including a person or a computer.

Although ordinal numbers such as first, second, and the like can, in some situations, relate to an order; as used in this document ordinal numbers do not necessarily imply an order. For example, ordinal numbers can be merely used to distinguish one item from another. For example, to distinguish a first event from a second event, but need not imply any chronological ordering or a fixed reference system (such that a first event in one paragraph of the description can be different from a first event in another paragraph of the description).

The foregoing description is intended to illustrate but not to limit the scope of the invention, which is defined by the scope of the appended claims. Other embodiments are within the scope of the following claims.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user can provide input to the computer. Other kinds of devices can be used to provide for interaction with a user as well. For example, feedback provided to the user can be any form of sensory feedback, such as for example visual feedback, auditory feedback, or tactile feedback; and input from the user can be received in any form, including, but not limited to, acoustic, speech, or tactile input.

The embodiments set forth in the foregoing description do not represent all embodiments consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the embodiments described above can be directed to various combinations and sub-combinations of the disclosed features and/or combinations and sub-combinations of several further features disclosed above. In addition, the logic flows depicted in the accompanying figures and/or described herein do not necessarily require the particular order shown, or sequential order, to achieve desirable results. Other embodiments can be within the scope of the following claims, as well as other claims which are supported by the subject disclosure.

What is claimed:

1. An apparatus for monitoring and/or performing a diagnosis, comprising
    a first implantable device for measuring a property of a first tissue in a body and having a housing, the housing including:
        a first processing circuitry for causing the first implantable device to measure the property of the first tissue using at least one of the following: an RF measurement of the property of the first tissue or an analysis of a signal reflected from the first tissue, wherein the signal is transmitted by the first implantable device toward the first tissue;
        a second implantable device for measuring a property of a second tissue in the body and having a housing, the housing including a second processing circuitry for causing the second implantable device to measure the property of the second tissue using at least one sensor;
        the second implantable device is communicatively coupled to the first implantable device and provides information about the measured property of the second tissue to at least one of the following: the first implantable device and at least one processing device disposed externally to the body.

2. The apparatus according to claim 1, wherein the first implantable device includes a power source for powering the first implantable device.

3. The apparatus according to claim 2, wherein the first implantable device transmits energy to the second implantable device to power the second implantable device.

4. The apparatus according to claim 1, wherein the property of the first tissue is at least one of: a level of hydration of the first tissue, a dielectric property of the first tissue, and an radio frequency ("RF") measurement of the first tissue, and wherein the property of the second tissue is blood pressure.

5. The apparatus according to claim 1, wherein the first implantable device includes an antenna selected from a group consisting of: a dipole antenna, a wire loops antenna, a stent-based antenna, and a printed antenna.

6. The apparatus according to claim 1, wherein the first implantable device wirelessly communicates with the second implantable device.

7. The apparatus according to claim 1, wherein the first implantable device is connected with the second implantable device using a wire.

8. The apparatus according to claim 1, wherein the housing of the first implantable device contains the second implantable device, wherein a power source of the first implantable device powers the second implantable device.

9. The apparatus according to claim 1, wherein the second implantable device is selected from a group consisting of: pulmonary artery blood pressure sensor and a left atrium pressure sensor.

10. The apparatus according to claim 1, wherein the housings of the first and second implantable devices are manufactured from a biocompatible material.

11. The apparatus according to claim 1, wherein the second implantable device reflects at least one signal transmitted by the first implantable device, wherein the first implantable device receives the reflected signal.

12. The apparatus according to claim 11, wherein the second implantable device modulates the signal prior to reflecting the signal transmitted by the first implantable device.

* * * * *